US010307245B2

(12) United States Patent
Blacklidge

(10) Patent No.: US 10,307,245 B2
(45) Date of Patent: Jun. 4, 2019

(54) TENDON RETENTION DEVICE

(71) Applicant: PARAGON 28, INC., Englewood, CO (US)

(72) Inventor: Douglas K. Blacklidge, Zionsville, IN (US)

(73) Assignee: PARAGON 28, INC., Englewood, CO (US)

(*) Notice: Subject to any disclaimer, the term of this patent is extended or adjusted under 35 U.S.C. 154(b) by 0 days.

(21) Appl. No.: 15/687,450

(22) Filed: Aug. 26, 2017

(65) Prior Publication Data

US 2018/0055623 A1    Mar. 1, 2018

Related U.S. Application Data

(60) Provisional application No. 62/500,574, filed on May 3, 2017, provisional application No. 62/454,100, filed on Feb. 3, 2017, provisional application No. 62/379,789, filed on Aug. 26, 2016.

(51) Int. Cl.
| | |
|---|---|
| *A61F 2/08* | (2006.01) |
| *A61B 17/72* | (2006.01) |
| *A61B 17/68* | (2006.01) |
| *A61B 17/56* | (2006.01) |

(52) U.S. Cl.
CPC .......... *A61F 2/0811* (2013.01); *A61B 17/683* (2013.01); *A61B 17/7291* (2013.01); *A61B 2017/564* (2013.01); *A61B 2017/681* (2013.01); *A61F 2002/0823* (2013.01); *A61F 2002/0829* (2013.01); *A61F 2002/0858* (2013.01);

(Continued)

(58) Field of Classification Search
CPC ........ A61F 2/08; A61F 2/0811; A61B 5/4523; A61B 5/4533; A61B 17/1146
See application file for complete search history.

(56) References Cited

U.S. PATENT DOCUMENTS

| | | | |
|---|---|---|---|
| 5,707,373 | A | 1/1998 | Sevrain et al. |
| 5,980,557 | A | 11/1999 | Iserin et al. |
| 6,050,819 | A | 4/2000 | Robinson |

(Continued)

FOREIGN PATENT DOCUMENTS

FR    2928824 A1    9/2009

OTHER PUBLICATIONS

International Search Report and Written Opinion issued for related PCT Application No. PCT/US2017/048780 dated Nov. 21, 2017.

*Primary Examiner* — Jason-Dennis N Stewart
(74) *Attorney, Agent, or Firm* — Heslin Rothenberg Farley & Mesiti P.C.

(57) ABSTRACT

A device is provided for retaining a tendon, such as, but not limited to, a flexor digitorum tendon onto an associated bone such as, but not limited to, the plantar aspect of a proximal phalangeal base for correction of a toe contracture. The tendon retention device is defined by a tack and a sleeve. The tack is configured for press-fit or instrument aided reception into the tendon and associated bone to retain the tendon against the associated bone. The sleeve has an internally threaded bore for threaded reception onto a threaded shaft of the tack from the opposing side of the associated bone. The sleeve further has a head with an anti-loosening feature or anti-loosening features such as, but not limited to, tangs and/or cutouts, that engage the associated bone to aid in preventing the sleeve from working loose from the bone and/or unthreading from the tack.

17 Claims, 9 Drawing Sheets

(52) U.S. Cl.
CPC ............. *A61F 2002/0864* (2013.01); *A61F 2002/0882* (2013.01)

(56) References Cited

U.S. PATENT DOCUMENTS

| | | | |
|---|---|---|---|
| 6,231,606 B1 | 5/2001 | Graf et al. |
| 6,258,091 B1 | 7/2001 | Sevrain et al. |
| 6,302,887 B1 | 10/2001 | Spranza et al. |
| 6,383,187 B2 | 5/2002 | Tormala et al. |
| 6,464,713 B2 | 10/2002 | Bonutti |
| 6,517,543 B1 | 2/2003 | Berrevoets et al. |
| 6,589,244 B1 | 7/2003 | Sevrain et al. |
| 6,648,890 B2 | 11/2003 | Culbert et al. |
| 6,918,912 B2 | 7/2005 | Seemann |
| 7,074,203 B1 | 7/2006 | Johanson et al. |
| 7,578,825 B2 | 8/2009 | Huebner |
| 7,604,659 B2 | 10/2009 | Lee |
| 7,686,807 B2 | 3/2010 | Padget et al. |
| 7,833,255 B2 | 11/2010 | Chow et al. |
| 8,043,347 B2 | 10/2011 | Jiang et al. |
| 8,147,514 B2 | 4/2012 | Bonutti |
| 8,357,186 B2 | 1/2013 | Hadi |
| 8,632,570 B2 | 1/2014 | Biedermann et al. |
| 8,672,985 B2 | 3/2014 | Chow et al. |
| 8,845,699 B2 | 9/2014 | Bonutti |
| 8,858,634 B2 | 10/2014 | Lewallen |
| 8,968,374 B2 | 3/2015 | Hoof et al. |
| 9,011,503 B2 | 4/2015 | Duggal et al. |
| 9,017,404 B2 | 4/2015 | Champagne et al. |
| 9,089,377 B2 | 7/2015 | Brown et al. |
| 9,247,963 B2 | 2/2016 | Kollmer |
| 9,333,069 B2 | 5/2016 | Denham |
| 9,445,842 B2 | 9/2016 | Cianfrani et al. |
| 9,510,883 B2 | 12/2016 | Weiss et al. |
| 2009/0228049 A1 | 9/2009 | Park |
| 2014/0222087 A1 | 8/2014 | Greenberg et al. |
| 2016/0038186 A1 | 2/2016 | Herzog et al. |
| 2016/0135861 A1 | 5/2016 | Kollmer |

TENDON RETENTION DEVICE

CROSS-REFERENCE TO RELATED APPLICATIONS

This U.S. non-provisional patent application claims the benefit of and/or priority under 35 U.S.C. § 119(e) to U.S. provisional patent application Ser. No. 62/379,789 filed Aug. 26, 2016 titled "Tendon Fixation Device," U.S. provisional patent application Ser. No. 62/454,100 filed Feb. 3, 2017 titled "Tendon Fixation Device," and U.S. provisional patent application Ser. No. 62/500,574 filed May 3, 2017 titled "Tendon Fixation Device," the entire contents of each of which is specifically incorporated herein by reference.

FIELD OF THE INVENTION

The present invention relates to surgical devices for retention of human tendons to bones, and more specifically, to the internal retention of the flexor digitorum longus tendon to the plantar base of the proximal phalanx of a toe to correct alignment of a contracted toe (e.g. hammertoe or claw toe).

BACKGROUND OF THE INVENTION

The toes of the human foot are very commonly contracted. The contracture of a toe produces pain due to increased pressure at the plantar metatarsal head, the dorsal proximal interphalangeal joint, and the distal end of the toe. Procedures utilized to correct the deformity include tendon release, tendon transfer, partial joint (interphalangeal joint) resection (arthroplasty), and joint (interphalangeal joint) fusion (arthrodesis). For flexible deformities, tendon procedures are often utilized. With a reducible contracture of a toe, a transfer of the flexor digitorum longus tendon to the extensor tendon apparatus is often used with a variety of techniques. The contracted flexor digitorum longus tendon is released from its insertion on the base of the distal phalanx and it is transferred medial or lateral to the proximal phalanx and sutured to the extensor tendon apparatus dorsally with the tendon tensioned to correct the alignment of the toe. This releases the deforming force of the contracted flexor tendon on the interphalangeal joints while preserving the tendons ability to flex the metatarsophalangeal joint. Correcting the alignment can alleviate the pain associated with the contracture.

Current procedures are performed to facilitate a secure new insertion for the flexor digitorum longus tendon despite the new location being less than ideal. Procedures to transfer the flexor digitorum longus tendon within the toe all have the goal of plantar flexing of the proximal phalanx at the metatarsophalangeal joint while releasing the contracture of the interphalangeal joints. Unfortunately, current procedures do not provide insertion of the flexor digitorum longus tendon to the plantar base of the proximal phalanx where it can best serve its new purpose. With attachment of the transferred flexor digitorum longus tendon to a location other than the plantar base of the proximal phalanx, metatarsophalangeal joint instability can persist, and transverse deviation of the toe can be exacerbated. The tendon is not routinely attached to its ideal new insertion due to technical difficulties and inadequate fixation methods.

Rerouting the flexor digitorum longus tendon through a dorsal to plantar drill hole in the proximal portion of the proximal phalanx is a procedure option, but this creates a large hole subject to fracture. The procedure is also technically difficult.

During a direct repair of a plantar metatarsophalangeal joint capsule (plantar plate) rupture, the flexor digitorum longus tendon is often used to reinforce the repair. The tendon is secured to the plantar base of the proximal phalanx with transosseus suturing or a small tendon anchor. The bone of the proximal phalangeal base is small and using the currently available tendon suture anchors is difficult—especially considering the challenge of appropriately tensioning the tendon while trying to secure it into its new insertion with suture. The aging population and associated osteopenia adds to the difficulty of attaining secure tendon to bone fixation. Other than a direct plantar metatarsophalangeal joint ligament repair type procedure, most efforts to simply realign a contracted toe are from dorsal, so the plantar base of the proximal phalanx is not exposed. If a secure means of fixation for the flexor digitorum longus tendon under appropriate tension for correcting a contracted toe could be done efficiently, and reproducibly, the approach to reconstructing the common deformity could be vastly improved.

It is therefore an object of the present invention to provide retention between a flexor digitorum longus tendon and the plantar aspect of a proximal phalangeal base for the correction of a toe contracture.

It is also an object of the present invention to provide retention between a flexor digitorum brevis tendon and associated foot bone.

It is further an object of the present invention to provide retention between a tendon/ligament and associated bone in various parts of the body.

SUMMARY OF THE INVENTION

In view of the need to provide better retention, fixation or securement between a tendon and an associated bone, such as, but not limited to, the flexor digitorum longus tendon and the plantar aspect of a proximal phalangeal base for the correction of a toe contracture, the current tendon retention, fixation, or securing device (tendon retention device) has been specifically designed. The tendon retention device provides secure retention or fixation of an appropriately tensioned tendon, such as but not limited to, the flexor digitorum longus tendon into an insertion site such as, but not limited to, on the plantar base of the proximal phalanx through incorporation of innovative threaded fixation and bone retention.

The tendon retention device is defined by a first component and a second component, the nomenclature first and second being arbitrary. The first component may be considered a tack while the second component may be considered a sleeve. The tack is configured for press-fit or instrument aided reception into the tendon and adjacent bone to retain the tendon against the adjacent bone. The sleeve has an internally threaded bore for threaded reception onto a threaded shaft of the tack from the opposing side of the adjacent bone. The sleeve further has a head with an anti-loosening feature or anti-loosening features such as, but not limited to, tangs and/or cutouts, that engage the bone to help prevent the sleeve from working loose and/or unthreading from the bone/tack.

The tack of the present tendon retention device is characterized by a head with a central, threaded shaft and a rough or projection-laden tendon contact surface situated on the side of the shaft that presses against the tendon to secure the tendon to the adjacent bone. The tack may further include a threaded hole at its bottom that allows the tack to be threaded onto an instrument to aid in installation. The threaded shaft extends from a cylindrical shank having a diameter that is preferably, but not necessarily, greater than the diameter of the threaded shaft, the transition between the cylindrical shank and the threaded shaft defining an angled surface. The threaded shaft has a preferably, but not necessarily, generally planar upper surface, however, other configurations such as, but not limited to, conical or pointed, may be used.

The sleeve is characterized by a tubular body having a head at one end preferably, but not necessarily, configured for instrument aided threading onto the threaded shaft of the tack, the head having one or more anti bone loosening features (anti-loosening features) that grip the bone to help prevent the sleeve from loosening from the bone and/or unthreading from the tack. In one form, the head has radially extending anti-loosening tangs defining pockets for gripping the bone, and an interior that is at least partially threaded to threadedly engage the threaded shaft of the tack. The interior preferably, but not necessarily, includes headroom distal to the threaded interior portion to accommodate bones of varying heights while using the same size tack.

In preparation of securing the tendon to the new insertion, the shaft is pushed and/or threaded through the flexor digitorum longus tendon once the tendon has been pierced with a scalpel, and the adjacent bone (phalange). The toe deformity is corrected manually, appropriately tensioning the tendon, then threading the sleeve through a bore in the bone, and threadedly onto the threaded shaft of the tack until the tendon is appropriately compressed.

In broad terms, a form of the tendon retention device is a rigid tendon to bone retention/fixation device with a headed tack having a rough surface on the head surrounding a threaded shaft to engage the tendon. Inserted from the opposite side of the bone is a headed tube of an internally threaded sleeve with radially extending tangs defining configured pockets, the tube threadedly received onto the threaded shaft of the tack and thus received into the bone.

Because of the design of the tack and sleeve, the present tendon retention device can accommodate a range of bone heights. Moreover, different sizes of tacks and/or sleeves can accommodate a wide variety of bone heights.

Further aspects of the invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

For instance, the present tendon retention device may also be used for the flexor digitorum brevis as well as elsewhere in the body for tendon/ligament fixation to bone.

BRIEF DESCRIPTION OF THE DRAWINGS

The features of the present invention will be better understood by reference to the accompanying drawings which illustrate a form of the present invention, wherein.

It should be appreciated that dimensions of the components, structures, and features of the present tendon retention device can be altered as desired.

DETAILED DESCRIPTION OF THE INVENTION

Figure 1:
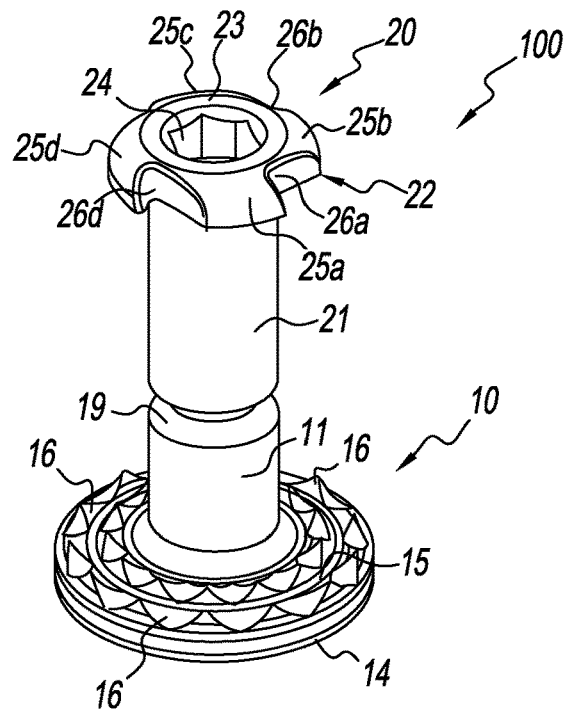
FIG. 1 is an isometric view of an exemplary form of a tendon retention device fashioned in accordance with the present principles.
Figure 2:
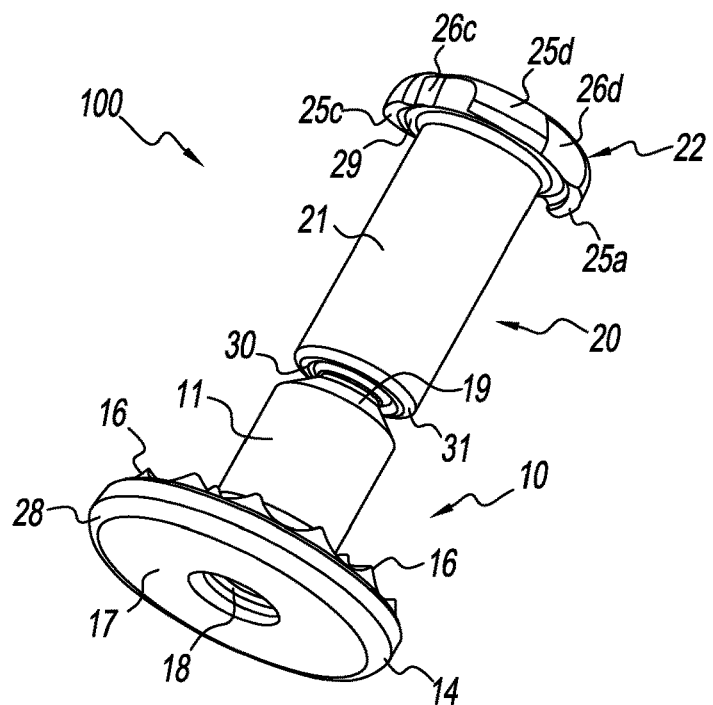
FIG. 2 is another isometric view of the tendon retention device of FIG. 1.
Figure 3:
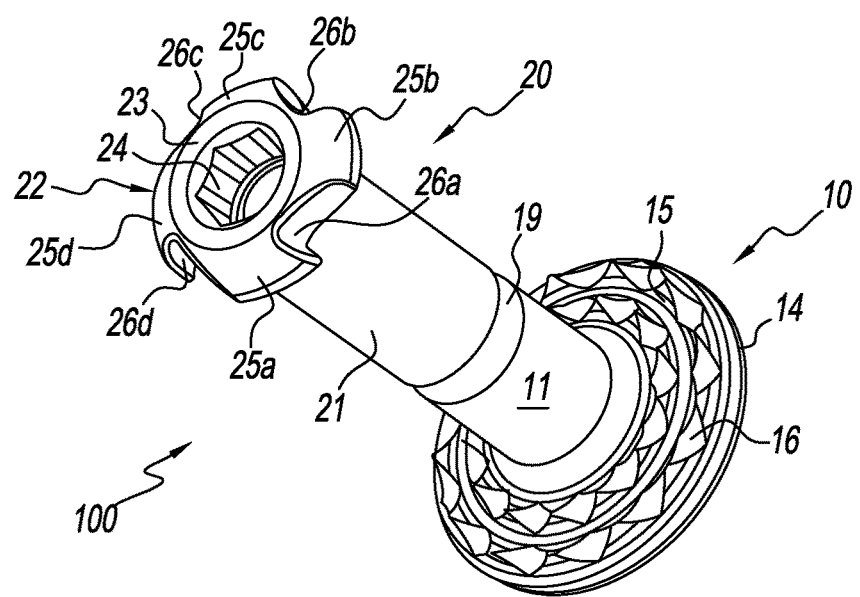
FIG. 3 is another isometric view of the tendon retention device of FIG. 1.
Figure 4:
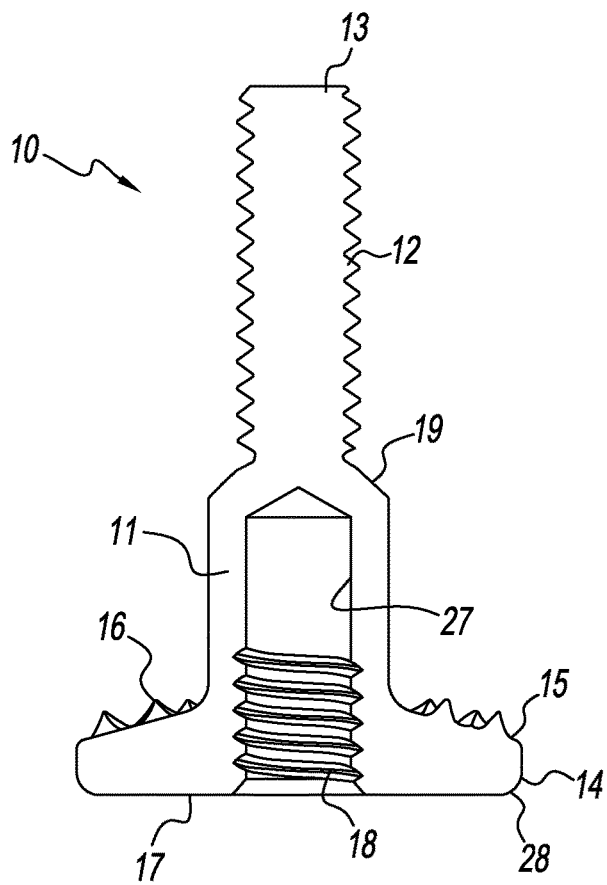
FIG. 4 is a sectional side view of a tack of the tendon retention device of FIG. 1.
Figure 5:
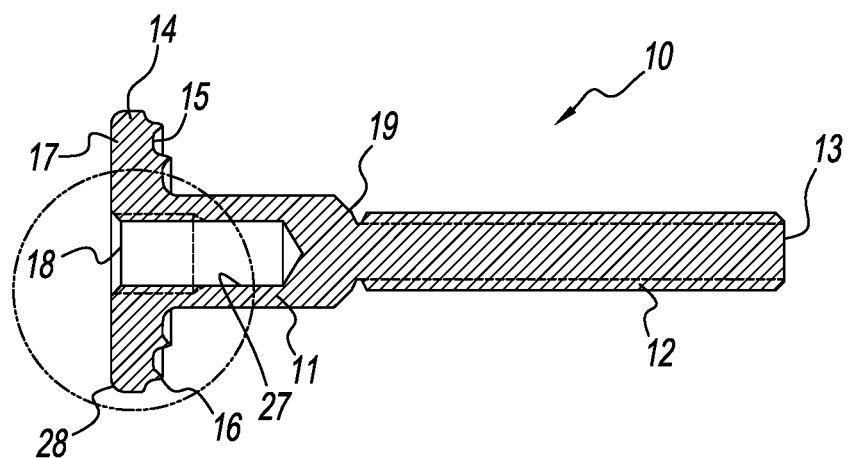
FIG. 5 is another sectional view of the tack of the tendon retention device of FIG. 1.
Figure 6:
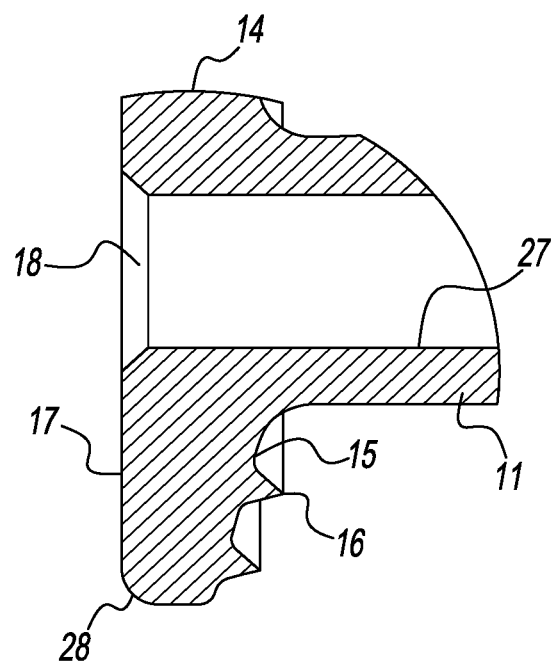
FIG. 6 is an enlarged view of a portion of the tack of FIG. 5 taken along circle 6 thereof.
Figure 7:
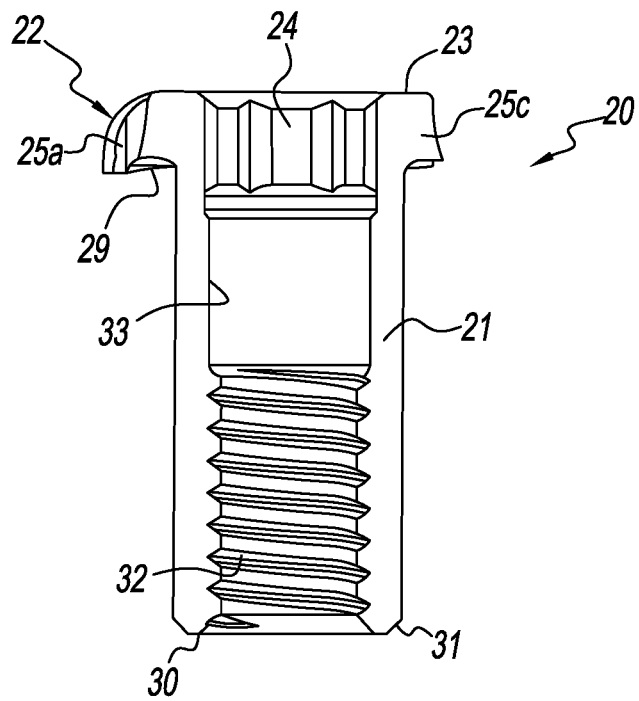
FIG. 7 is a sectional side view of a sleeve of the tendon retention device of FIG. 1.
Figure 8:
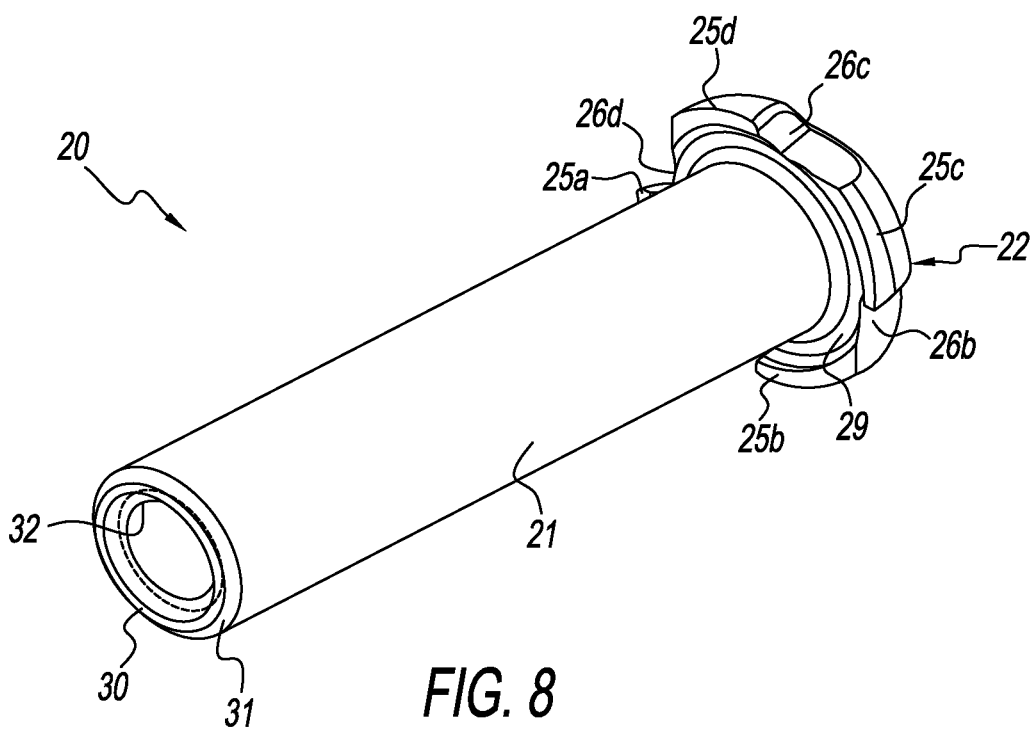
FIG. 8 is an isometric view of the sleeve of FIG. 7.
Figure 9:
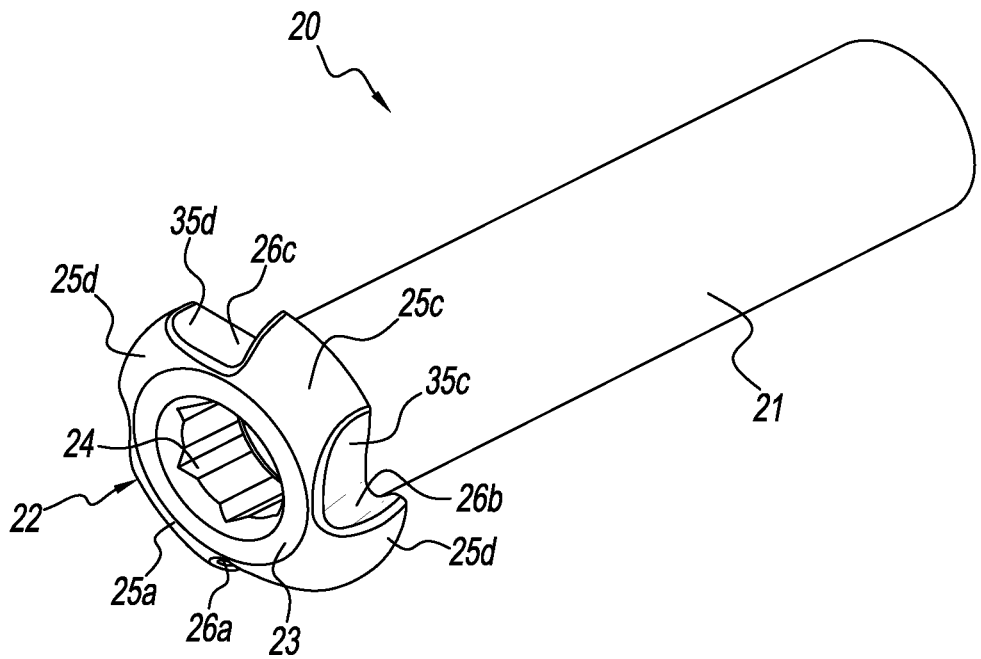
FIG. 9 is another isometric view of the sleeve of FIG. 7.
Figure 10:
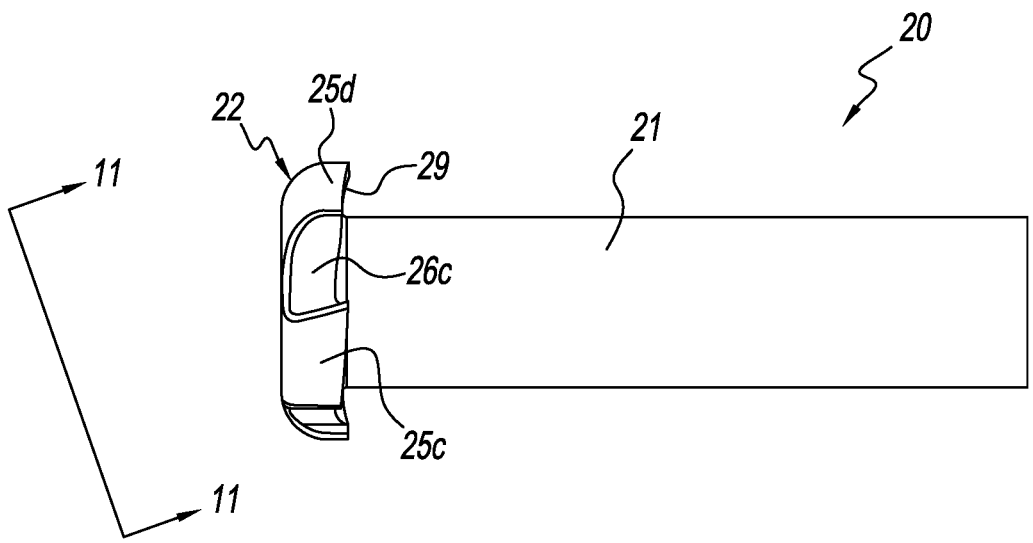
FIG. 10 is a side view of the sleeve of FIG. 7.
Figure 11:
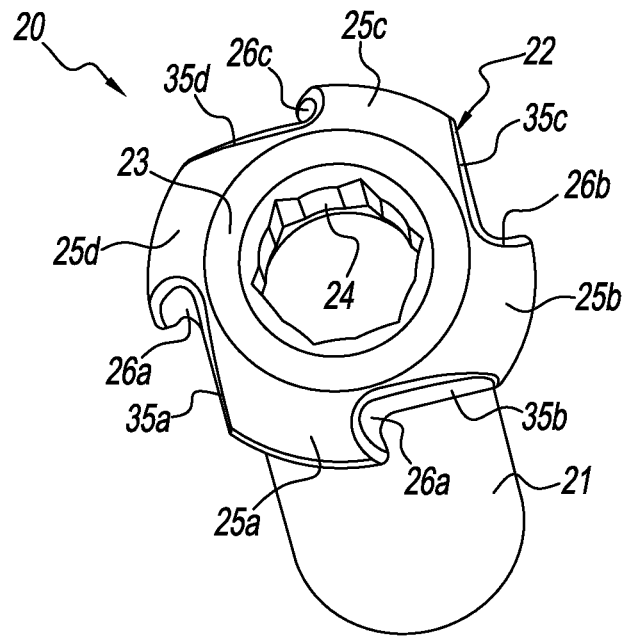
FIG. 11 is a top side view of the sleeve of FIG. 7.
Figure 12:
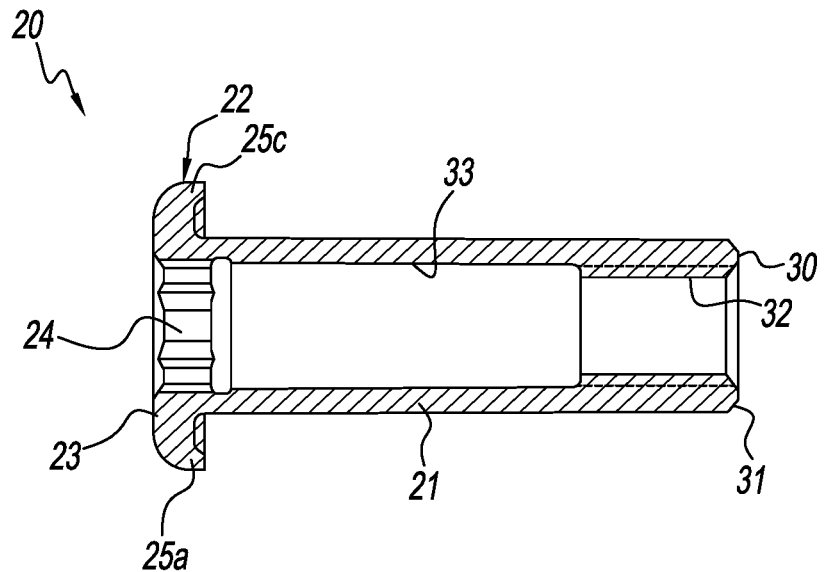
FIG. 12 is a sectional side view of the sleeve of FIG. 7.
Figure 13:
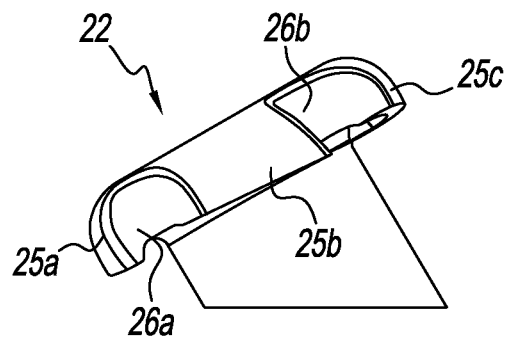
FIG. 13 is an enlarged sectional side view of the head of the sleeve of FIG. 7.
Figure 14:
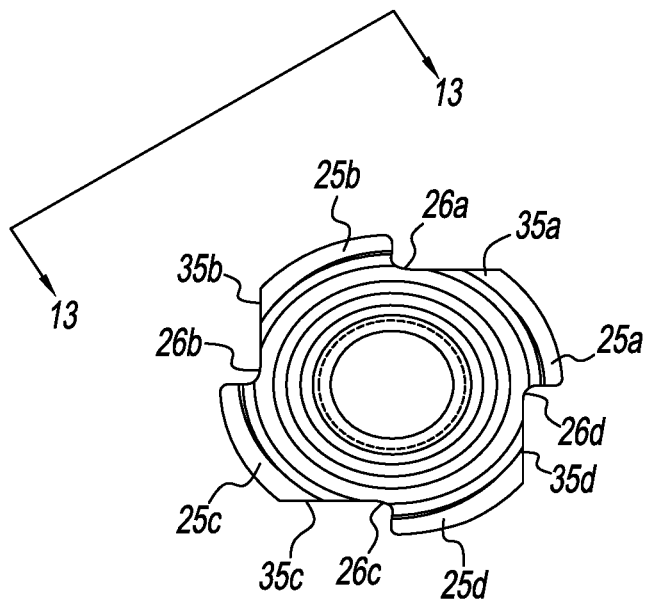
FIG. 14 is a top view of the head of the sleeve of FIG. 13.
Figure 15:
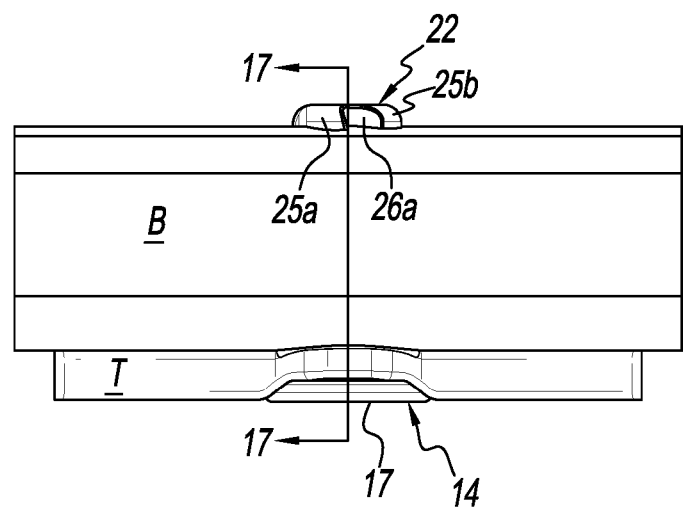
FIG. 15 is a side view of a portion of a proximal phalange and associated flexor digitorum longus tendon secured with the present tendon retention device.
Figure 16:
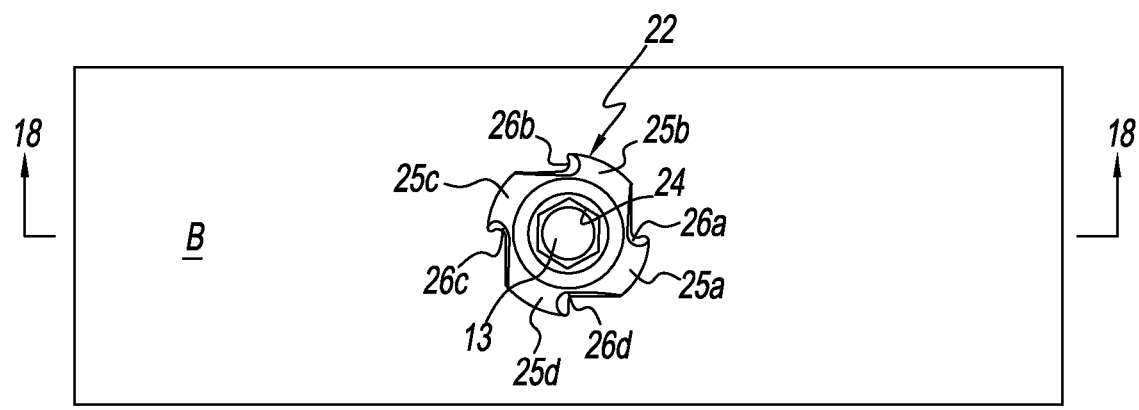
FIG. 16 is a top view of the portion of a proximal phalange and associated flexor digitorum longus tendon secured with the present tendon retention device.
Figure 17:
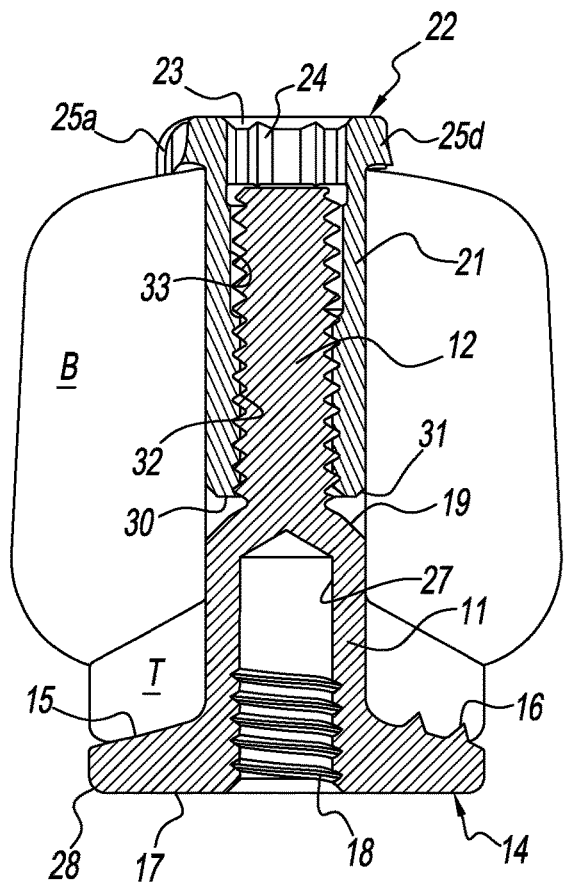
FIG. 17 is a sectional view of the portion of a proximal phalange and associated flexor digitorum longus tendon secured with the present tendon retention device taken along line 17-17 of FIG. 15.
Figure 18:
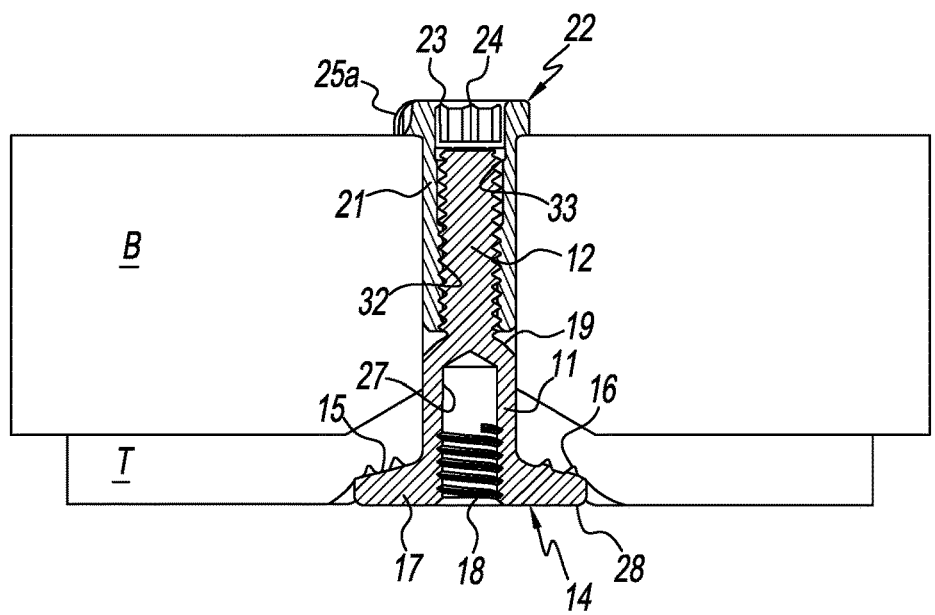
FIG. 18 is a sectional view of the portion of a proximal phalange and associated flexor digitorum longus tendon secured with the present tendon retention device taken along line 18-18 of FIG. 16.

Referring to FIGS. 1-18, there is shown an exemplary form of a tendon retention of fixation device or implant (tendon retention device), generally designated 100, fashioned in accordance with the present principles, for retention, fixation, and/or securement of and/or between a tendon, such as, but not limited to a flexor digitorum longus tendon and an associated bone, such as, but not limited to, the plantar aspect of a proximal phalangeal base (bone) particularly, but not necessarily, for the correction of a toe contracture. The present tendon retention device 100 may be used for retention, fixation, and/or securement of other tendons to other bones such as, but not limited to, bones of the hand. The tendon retention device 100 is preferably, but not necessarily, made of a biocompatible metal such as titanium, stainless steel, an alloy, or the like, or other biocompatible material such as plastic, ceramic or the like. The tendon retention device 100 is characterized by a first component 10 and a second component 20, the nomenclature first and second being arbitrary. The first component 10, without being restrictive, may be termed a tack, while the second component 20, without being restrictive, may be termed a sleeve 20. When implanted, the sleeve 20 is received onto the tack 10.

FIGS. 1-18 show various views of the tendon retention device 100 assembled, implanted with respect to a tendon T and associated/adjacent bone B, and separately—the two components, tack 10 and sleeve 20. Any dimensions, angles and/or the like depicted in the figures, while preferred, are illustrative and not necessarily dispositive. Other dimensions, angles and/or the like can be used and are contemplated.

The tack 10 is characterized by a generally disk-shaped base 14, although other shapes may be used, having a generally planar upper side, face or surface 17 and a sloped or angled lower side, face or surface 15, the nomenclature upper and lower being arbitrary. An internally threaded bore, hole, cavity or depression 18 is formed in the upper side 17. The threaded bore 18 is configured to receive a like threaded instrument or tool (not shown) for inserting or aiding in the insertion, installation or implantation of the tack 10 into a tendon and bone. The tack 10 further includes a shank or the like 11 that extends generally transverse from the lower side 15 of the head 14. The shank 11 has a first diameter. A threaded shaft 12 with a blunt end 13 extends from the shank 11, the threaded shaft 12 having a second diameter (including the external threading) that is less than the first diameter of the shank 11. An angled portion 19 is preferably, but not necessarily, provided at the transition between the shank 11 and threaded shaft 12, i.e. as a transition between the larger diameter section comprising the shank 11 and the smaller diameter section comprising the threaded shaft 12.

The lower side 15 of the head 14 includes a rough, coarse, bumpy, or textured (collectively, textured) surface, shown as a plurality of bumps, protrusions, spikes or the like (collectively, protrusions) 16 situated about the lower side 15. Other types of textured surfaces may be used including coatings, treatments or otherwise. Moreover, while the protrusions 16 are situated in two rings about the shank 11, other patterns or no patters of protrusions 16 may be used.

The sleeve 20 is characterized by a generally tubular body 21 having a cap, head or top (head) 22 with a generally planar upper surface 23. A socket 24 is provided in the head 22 that is configured to receive a like configured installation tool or instrument (not shown). While the socket 24 is shown as hexagonal, other configurations may be used. The head 22 has one or more anti-loosening features. To this end a plurality of tangs 25a-d radially project from the outer periphery of the head 22. The tangs 25a-d define a plurality of pockets or cutouts 26a-d with a pocket 26 between each tang 25. Each tang 25a-d has a respective flat 35a-d and is generally circumferentially arced in a counterclockwise direction relative to a top view thereof. The configuration of the tangs 25a-d, pockets 26a-d, and flats 35a-d allows generally unrestricted rotation of the head 22 relative to the bone during clockwise threaded rotational installation of the sleeve 20 onto the tack 10 (as view from the top thereof), but provides restricted counterclockwise rotational movement of the head 22 (as view from the top thereof) through gripping of the bone by the head anti-loosening structure (tangs, pockets and/or flats) should the sleeve 20 undergo de-threading or loosening from the tack 10. The cap 22 also defines an undersurface or overhang 29 that may be configured to aid in the anti-loosening feature(s).

The tubular body 21 has an interior bore that extends from the socket 24 to a lower opening 32 at a bottom 30 of the tubular body 21. The lower opening 32 is threaded complementary to the external threading of the threaded shaft 12 of the tack 10 such that the sleeve 20 can be threadedly received on the tack 10. An upper portion 33 of the bore 28 axially between the socket 24 and the threaded opening 32 is unthreaded. The length of the upper portion 33 allows the sleeve 20 to accommodate various sizes of bones. The outer circumference of the bottom 30 has a taper 31.

FIGS. 15-18 show several views of the present tendon retention device 100 implanted or installed into a bone B and associated tendon T in order to affix, secure or hold the tendon T to/onto the bone B. The tack 10 and the sleeve 20 are made in a variety of sizes to retain, affix, secure or hold various sized tendons to various sized bones to accommodate a range of anatomical sizes. Thus, varying height of bones can be accommodated by various "sizes" of the first component 10 and/or the second component 20.

In an exemplary "size 1" tendon retention device, a minimal bone height (6.75) is accomplished by threading the sleeve 20 completely onto the threaded shaft 12 of the tack 10 such that the end of the sleeve 20 bottoms out on the taper (ledge) 19 of the tack 10 between the shank 11 and the threaded shaft 12. A maximum bone height (8.50) is accomplished by threading the sleeve 20 partially onto the threaded shaft 12 of the tack 10. An exemplary "size 2" tendon retention device is used with a minimal bone height (8.60) by threading the sleeve 20 completely onto the threaded shaft 12 of the tack 10 such that the end of the sleeve 20 bottoms out on the taper (ledge) 19 of the tack 10 between the shank 11 and the threaded shaft 12. A maximum bone height (11.50) is accomplished by threading the sleeve 20 partially onto the threaded shaft 12 of the tack 10. An exemplary "size 3" tendon retention device is used with a minimal bone height (11.6) by threading the sleeve 20 completely onto the threaded shaft 12 of the tack 10 such that the end of the sleeve 20 bottoms out on the taper (ledge) 19 of the tack 10 between the shank 11 and the threaded shaft 12. A maximum bone height (16.5) is accomplished by threading the sleeve 20 partially onto the threaded shaft 12 of the tack 10. An exemplary "size 4" tendon fixation device consisting of a "size 4" tack 10 and a "size 3" sleeve 20 may be used with a minimal bone height (16.60) by threading the sleeve 20 completely onto the threaded shaft 12 of the tack 10 such that the end of the sleeve 20 bottoms out on the taper (ledge) 19 of the tack 10 between the shank 11 and the threaded shaft 12. A maximum bone height (21.00) is accomplished by threading the sleeve 20 partially onto the threaded shaft 12 of the tack 10.

It can be seen from the Figures how the present tendon retention device is used to retain, affix, fix, secure, or otherwise hold the tendon onto the bone. However, in preparation of securing the tendon to the new insertion, the tendon is pierced by a scalpel (or other instrument) and a bore is drilled in the bone. The shaft of the tack is pushed through the tendon and the tendon is appropriately tensioned. The sleeve is threaded onto the threaded shaft of the tack until the tendon is appropriately compressed.

What is claimed is:

1. A device for retaining a tendon onto an associated bone, the device comprising:
   a first component configured for insertion into and through a tendon and into an associated bone, the first component having a base defining a sloped upper side and a lower side, texturing on the sloped upper side of the base, a shank of a first diameter extending from the upper side of the base and having an upper end distal to the base, and an externally threaded shaft extending from the upper end of the shank and having a second diameter that is less than the first diameter of the shank; and
   a second component configured for insertion into and through the associated bone and onto the first component, the second component having a tubular body defining a first end and a second end, an internally threaded bore extending into the tubular body from the first end thereof and sized to threadedly engage the externally threaded shaft of the first component, and a head on the second end of the tubular body, the head having non-threaded bone engagement features that allow the second component to be threadedly received onto the first component but disallow disengagement of the second component from the first component.

2. The device of claim 1, wherein the non-threaded bone engagement features comprise:
a plurality of tangs radially extending from a periphery of the head and defining a plurality of pockets between the tangs.

3. The device of claim 1, wherein the texturing on the sloped upper side of the base comprises a plurality of projections.

4. The device of claim 1, further comprising:
a configured bore in an upper surface of the head of the second component.

5. The device of claim 1, further comprising:
an angled transition disposed between the upper end of the shank and the externally threaded shaft.

6. The device of claim 1, wherein:
the shank and externally threaded shaft of the first component are cylindrical; and
the tubular body of the second component is cylindrical.

7. The device of claim 1, wherein an upper end of the externally threaded shaft of the first component is planar.

8. The device of claim 1, further comprising:
an internally threaded hole on the lower side of the base.

9. A device for securing soft-tissue to a bone comprising:
a tack configured for insertion into and through a portion of soft tissue and into a portion of a bone, the tack having a round base defining a sloped upper side and a planar lower side, texturing on the sloped upper side of the rounded base, a shank of a first diameter extending from the upper side of the rounded base and having an upper end distal to the rounded base, and an externally threaded shaft extending from the upper end of the shank and having a second diameter that is less than the first diameter of the shank; and
a sleeve configured for insertion into and through the portion of the bone and onto the tack, the sleeve having a tubular body defining a first end and a second end, an internally threaded bore extending into the tubular body from the first end thereof and sized to threadedly engage the externally threaded shaft of the tack, and a head on the second end of the tubular body, the head having non-threaded bone engagement features that allow the second component to be threadedly received onto the tack but disallow disengagement of the second component from the tack.

10. The device of claim 9, wherein the non-threaded bone engagement features comprise:
a plurality of tangs radially extending from a periphery of the head and defining a plurality of pockets between the tangs.

11. The device of claim 9, wherein the texturing on the sloped upper side of the round base comprises a plurality of projections.

12. The device of claim 9, further comprising:
a configured bore in an upper surface of the head of the sleeve.

13. The device of claim 9, further comprising:
an angled transition disposed between the upper end of the shank and the externally threaded shaft.

14. The device of claim 9, wherein:
the shank and externally threaded shaft of the tack are cylindrical; and
the tubular body of the sleeve is cylindrical.

15. The device of claim 9, wherein an upper end of the externally threaded shaft of the first component is planar.

16. The device of claim 9, further comprising:
an internally threaded hole on the lower side of the round base.

17. A method for securing a flexor digitorum longus tendon to a plantar aspect of a proximal phalangeal bone for the correction of a toe contracture comprising the steps of:
piercing the flexor digitorum longus tendon by a sharp instrument);
drilling a bore in the proximal phalangeal bone;
providing a retention device comprising:
a tack configured for insertion into and through the flexor digitorum tendon and into a plantar aspect of the proximal phalangeal bone, the tack having a round base defining a sloped upper side and a planar lower side, texturing on the sloped upper side of the rounded base, a shank of a first diameter extending from the upper side of the rounded base and having an upper end distal to the rounded base, and an externally threaded shaft extending from the upper end of the shank and having a second diameter that is less than the first diameter of the shank; and
a sleeve configured for insertion into and through the proximal phalangeal bone and onto the tack, the sleeve having a tubular body defining a first end and a second end, an internally threaded bore extending into the tubular body from the first end thereof and sized to threadedly engage the externally threaded shaft of the tack, and a head on the second end of the tubular body, the head having non-threaded bone engagement features that allow the second component to be threadedly received onto the tack but disallow disengagement of the second component from the tack;
pushing the externally threaded shaft of the tack through the flexor digitorum tendon;
tensioning the flexor digitorum tendon;
threading the sleeve onto the threaded shaft of the tack until the flexor digitorum tendon is appropriately compressed.

* * * * *